US00PP26373P3

(12) United States Plant Patent
Bolinder

(10) Patent No.: US PP26,373 P3
(45) Date of Patent: Feb. 2, 2016

(54) ***CLEMATIS* PLANT NAMED 'BLUE GLOSS'**

(50) Latin Name: ***Clematis* hybrid**
Varietal Denomination: BLUE GLOSS

(71) Applicant: Kjell Bolinder, Hoganas (SE)

(72) Inventor: Kjell Bolinder, Hoganas (SE)

( * ) Notice: Subject to any disclaimer, the term of this patent is extended or adjusted under 35 U.S.C. 154(b) by 128 days.

(21) Appl. No.: 13/999,900

(22) Filed: Mar. 31, 2014

(65) Prior Publication Data

US 2015/0282407 P1 Oct. 1, 2015

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Annette Para
(74) *Attorney, Agent, or Firm* — Cassandra Bright

(57) ABSTRACT

A new and distinct *Clematis* hybrid named 'BLUE GLOSS' is disclosed, characterized by a distinctive silvery violet-blue flowers, and dense, shrubby plant form. Plant habit is well suited for container plantings. Semi-double flowers in Spring (May/June), single flowers August/September. The new cultivar is a *Clematis* typically suited for ornamental container and landscape use.

2 Drawing Sheets

Latin name of the genus and species: *Clematis* hybrid.
Variety denomination: 'BLUE GLOSS'.

BACKGROUND OF THE INVENTION

The new cultivar is the result of chance discovery in Hoganas Sweden. The inventor is Kjell Bolinder, a citizen of Sweden The new variety was discovered as a single seedling, of unknown parentage. The discovery was made in June 2003.

After selecting and isolating the new cultivar, asexual reproduction of the new cultivar 'BLUE GLOSS' was first performed in Sweden, at a hobbyist nursery by vegetative cuttings in June 2007. 'BLUE GLOSS' has since produced multiple generations, and has shown that the unique features of this cultivar are stable and reproduced true to type.

SUMMARY OF THE INVENTION

The cultivar 'BLUE GLOSS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BLUE GLOSS.' These characteristics in combination distinguish 'BLUE GLOSS' as a new and distinct *Clematis* cultivar:

1. Silvery violet-blue flowers.
2. Stamens are white.
3. Semi-double flowers in Spring (May/June), single flowers August/September.
4. Dense, bushy plant habit.
5. Suitability for container culture.

PARENTAL COMPARISON

Parents are unknown to the inventor.

COMMERCIAL COMPARISON

Plants of the new cultivar 'BLUE GLOSS' are similar to the commercial variety *Clematis* hybrid 'Beauty of Worcester' unpatented, in most horticultural characteristics. However, the new variety differs from 'Beauty of Worcester' in the following:

1. The new variety has larger flowers.
2. The new variety has a more silvery flower color, due to more violet-blue, rather than lavender coloration.
3. The new variety is denser and shrubbier than 'Beauty of Worcester'.

The new variety can also be compared to *Clematis* 'Lasurstern', differing in the following characteristics:

1. The new variety has smaller flowers.
2. The new variety has a lighter flower color.
3. The new variety is denser and shrubbier than 'Lasurstern'.

BRIEF DESCRIPTION OF THE PHOTOGRAPHS

Figure 1:
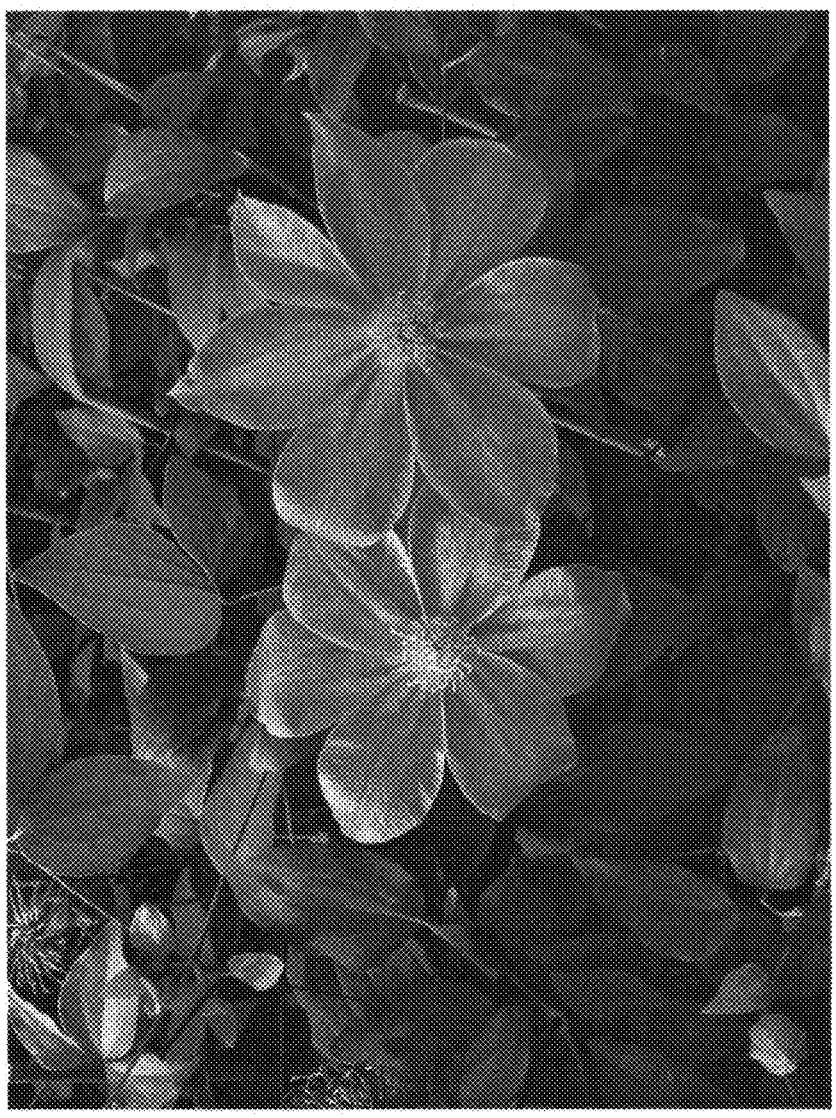

The accompanying photograph in FIG. 1 illustrates in full color a typical single flower of 'BLUE GLOSS' grown outdoors in Germany.

Figure 2:
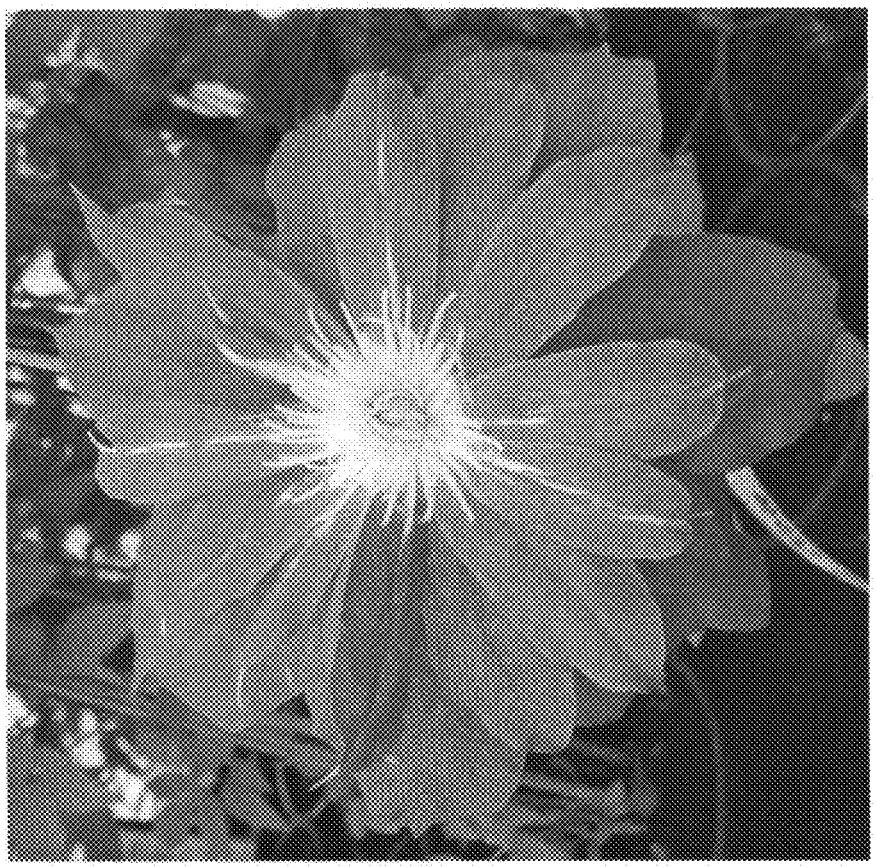

FIG. 2 illustrates in full color a typical semi-double of the flower.

DETAILED BOTANICAL DESCRIPTION

In the following description, color references are made to The Royal Horticultural Society Colour Chart 2007, except where general terms of ordinary dictionary significance are used. The following observations and measurements describe 'BLUE GLOSS' plants grown outdoors in British Columbia, Canada. Measurements were taken in May. The growing temperature ranged from 0° C. to 25° C. at night to 0° C. to 30° C. during the day. No artificial light, photoperiodic treatments or chemical treatments were given to the plants. Plants were pinched twice. Measurements and numerical values represent averages of typical flowering types.

Botanical classification: *Clematis* hybrid 'BLUE GLOSS'.
Age of the plant described: Approximately 8 months.
Container size of the plant described: Growing in the ground.

PROPAGATION

Typical method: Vegetative cuttings.
Time to initiate rooting: Approximately 20 days at 21° C. or higher.
Time to produce a rooted plantlet: Approximately 20 days at 20° C. or higher.
Root description: Fine, fibrous.

PLANT

Growth habit: Shrubby vine.
Height: Approximately 200 to 250 cm, measured from the soil line of the pot after approximately 8 months.
Plant spread: Approximately 180 cm.
Growth rate: Rapid during active growing season in Spring. Typically short for the first 2 years, growing faster with more age.
Branching characteristics: One main stem, easily making side branches from a pinch.
Length of main stem: Approximately 270 cm.
Diameter of main stem: Approximately 0.2 to 0.5 cm.
Main stem color: Near RHS Greyed-Green 165B, heavily flushed Greyed-Red 181B.
Main stem texture: Glabrous.
Internode length: Varies from 7 to 18 cm.
Strength: Strong, flexible, semi-woody.

FOLIAGE

Leaf:
*Arrangement*.—Opposite, ternate.
*Overall leaf length*.—Approximately 10 to 14 cm.
*Overall leaf diameter*.—Approximately 7 to 9 cm.
*Leaflets*.—Average Length: approximately 5 to 8 cm. Average Width: approximately 3 to 4.5 cm. Shape of blade: Oblong. Apex: Acute. Base: Cordate.
*Attachment*.—Stalked.
*Margin*.—Entire.
*Texture of both surfaces*.—Slightly bullate.
*Color*.—Young foliage upper side: Near RHS Green 137A. Young foliage under side: Near RHS Green 137C. Mature foliage upper side: Near RHS Green 137A. Mature foliage under side: Near RHS Green 137C.
*Venation*.—Type: Pinnate. Venation color upper side: Near RHS Yellow-Green 145C. Venation color under side: Near RHS Yellow-Green 145B.
Petiole:
*Length*.—Approximately 2.0 to 5.0 cm.
*Diameter*.—Approximately 0.2 cm.
*Texture*.—Smooth.
*Color*.—Near RHS Greyed-Red 181B on upperside, Green 137B on lower surface.

FLOWER

Bloom period:
*Natural season*.—May through June, and again August through September.
Inflorescence type and habit: Single occurring, axillary. Flowers facing outward and slightly upward. Semi-double flowers in Spring (May/June), single flowers August/September.
Rate of flower opening: Approximately 7 days from bud to fully opened flower.
Flower longevity on plant: Approximately 8 to 15 days, after fully opened. Self-cleaning.
Inflorescence size:
*Diameter*.—Approximately 14 to 16 cm.
*Depth*.—Approximately 4.5 cm.
Single flowers:
*Corolla*.—Tepal arrangement: slightly overlapping single whorl. Quantity: Typically 8 per flower. Size: Length: Approximately 4.5 to 7.0 cm. Width: Approximately 1.5 to 3.0 cm. Margin: Slightly curved. Apex: Acuminate. Base: Blunt. Texture: Smooth.
*Color*.—Tepals: When opening: Upper surface: Near RHS Violet-Blue 96C. Center streak near Violet N87D. Lower surface: Near RHS Violet-Blue 96C. Fully opened: Upper surface: Near RHS Violet-Blue 96D. Center streak near Violet N87D. Lower surface: Near RHS Violet-Blue 96D. Ageing: Upper Surface: Near RHS Violet-Blue 97A. Lower Surface: Near RHS Violet-Blue 97A.
Semi-double flowers:
*Corolla*.—Tepal arrangement: Overlapping, typically 2 or 3 whorls. Quantity: Typically 24 per flower. Size: Length: Approximately 4 to 6.2 cm. Width: Approximately 2.0 to 3.0 cm. Margin: Slightly curved. Apex: Acuminate. Base: Blunt. Texture: Smooth.
*Color*.—Tepals: When opening: Upper surface: Near RHS Violet-Blue 92A. Lower surface: Near RHS Violet-Blue 92A. Fully opened: Upper surface: Near RHS Violet-Blue 92A. Center streak near Violet 92D. Lower surface: Near RHS Violet-Blue 92B. Ageing: Upper Surface: Near RHS Violet-Blue 92B Center streak near White N155A. Lower Surface: Near RHS Violet-Blue 92C.
*Bud*.—Shape: Conical. Length: Approximately 2.4 cm. Diameter: Approximately 1.7 cm. Color: Near RHS Violet-Blue 93C.
Peduncles:
*Length*.—Average 15 cm.
*Width*.—Approximately 1.5 cm.
*Angle*.—Average 45°.
*Strength*.—Flexible.
*Color*.—Near RHS Greyed-Red 181D.
Fragrance: None.

REPRODUCTIVE ORGANS

Stamens:
*Number*.—Average 40 per flower.
*Stamen color*.—Near White N155B.
*Anther length*.—Approximately 1.5 cm.
*Anther color*.—Near RHS Purple N79D.
*Anther shape*.—Oblong.
*Pollen quantity*.—Moderate.
*Pollen color*.—Near White N155C.
Pistil:
*Length*.—Approximately 2 cm.
*Style length*.—Approximately 0.6 to 0.8 cm.
*Stigma*.—Shape: Linear. Color: Near RHS Violet 84D.

OTHER CHARACTERISTICS

Seeds and fruits: Not observed to date.
Disease/pest resistance: Neither resistance nor susceptibility to normal diseases and pests of *Clematis* has been observed.
Temperature tolerance: Tolerates temperatures from approximately −20° C. to 45° C.

What is claimed is:

1. A new and distinct cultivar of *Clematis* hybrid plant named 'BLUE GLOSS' as herein illustrated and described.

* * * * *